United States Patent [19]

Haviv et al.

[11] Patent Number: 5,413,990
[45] Date of Patent: May 9, 1995

[54] N-TERMINUS MODIFIED ANALOGS OF LHRH

[75] Inventors: Fortuna Haviv, Deerfield, Ill.; Timothy D. Fitzpatrick, Boulder, Colo.; Rolf E. Swenson, Grayslake, Ill.; Charles J. Nichols, Greendale, Wis.; Nicholas A. Mort, Waukegan, Ill.

[73] Assignee: Tap Pharmaceuticals Inc., Deerfield, Ill.

[21] Appl. No.: 103,022

[22] Filed: Aug. 6, 1993

[51] Int. Cl.⁶ .............. A61K 37/00; A61K 37/02; C07K 5/00; C07K 7/00
[52] U.S. Cl. ....................... 514/15; 530/313; 530/328
[58] Field of Search ............. 514/15; 530/313, 328

[56] References Cited

U.S. PATENT DOCUMENTS

| | | | |
|---|---|---|---|
| 4,800,191 | 1/1989 | Schally et al. | 514/15 |
| 5,110,904 | 5/1992 | Haviv et al. | 530/313 |
| 5,171,835 | 12/1992 | Janaky et al. | 530/313 |
| 5,198,533 | 3/1993 | Schally et al. | 530/313 |

FOREIGN PATENT DOCUMENTS

| | | | |
|---|---|---|---|
| 0182262 | 5/1986 | European Pat. Off. | |
| 0413209 | 2/1991 | European Pat. Off. | |
| WO9106543 | 5/1991 | WIPO | C07D 294/14 |
| WO9213883 | 8/1992 | WIPO | C07K 7/20 |
| WO9217025 | 10/1992 | WIPO | H04N 5/253 |
| WO9222322 | 12/1992 | WIPO | A61K 39/00 |

*Primary Examiner*—Jill A. Warden
*Assistant Examiner*—Sheela J. Huff
*Attorney, Agent, or Firm*—Jerry F. Janssen

[57] ABSTRACT

Decapaptides substituted on the N-terminal nitrogen atom by acyl groups are potent antagonists of LHRH and are useful for suppressing the levels of sex hormones in mammals.

1 Claim, No Drawings

N-TERMINUS MODIFIED ANALOGS OF LHRH

TECHNICAL FIELD

The present invention relates to organic compounds having biological activity, to compositions containing the compounds, and to medical methods of treatment. More particularly, the present invention concerns certain N-terminus modified deca and undecapeptides having LHRH antagonist activity, pharmaceutical compositions containing the peptides, and a method of inhibiting LHRH activity in a mammal in need of such treatment.

BACKGROUND OF THE INVENTION

The gonadotropins: follicle stimulating hormone (FSH), luteinizing hormone (LH), and chorionic gonadotropin (CG), are required for ovulation, spermatogenesis, and the biosynthesis of sex steroids. A single hypothalamic hormone, gonadotropin-releasing hormone (GnRH, also known as luteinizing is hormone-releasing hormone, LHRH) is responsible for regulating the secretion of both FSH and LH in mammals.

The structure of LHRH was determined by A. V. Schally, et al., *Science,* 173:1036–1037 (1971) and shown to be the decapeptide (sequence ID No. 1).

5-Oxo-Pro-His
Trp-Ser-Tyr-Gly-Leu-Arg-Pro-GlyNH$_2$

Early attempts to prepare peptides having LHRH-like activity centered on the synthesis of compounds which were LHRH agonists. However, in 1976 it was found that while individual doses of LHRH stimulated the release of gonadotropin, the continuous administration of small doses of LHRH or chronic administration of LHRH agonists had the opposite effect. This finding stimulated research for the discovery of both agonist and antagonist analogs of LHRH as agents useful for regulating sex steroids in mammals. A considerable number of patents and articles in the open literature disclose analogs of LHRH which either act as agonists of LHRH (i.e. act to stimulate the release of LH and FSH) or as antagonists of LHRH (i.e. act to inhibit the release of LH and FSH). For the most part, these compounds contain nine or ten aminoacyl residues, substituting naturally-occurring or non-naturally-occurring amino acid residues at one or more positions in the natural sequence of LHRH. In some cases, active antagonists of LHRH have been reported which contain fewer than ten amino acid residues.

The literature has reported that LHRH antagonists are useful for the treatment of a variety of conditions in which the suppression of sex steroids plays a key role including contraception, delay of puberty, treatment of benign prostatic hyperplasia, palliative treatment or remission of hormonal-dependent tumors of the breast and ovaries, palliative treatment or remission of hormonal-dependent tumors of the prostate, the treatment of cryptoorchidism, hirsutism in women, gastric motility disorders, dysmenorrhea, and endometriosis.

SUMMARY OF THE INVENTION

The present invention provides, in its principle embodiment, a class of deca and undecapeptide antagonist analogs of LHRH which have been modified at the N-terminus by addition of either an acyl functional group or an acyl functional group together with an additional aminoacyl residue. The compounds of the present invention inhibit the secretion of gonadotropins by the pituitary gland and inhibit the release of steroids by the gonads.

In particular, the peptides of the present invention have the structure:

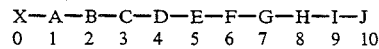

where the letters A through J represent aminoacyl residues and X represents an N-terminus-modifying acyl group. In accordance with the present invention X is an acyl group selected from the group consisting of $R^1$—CO—, $R^2(CH_2)_m$—CO—, and $R^3R^4N$—$(CH_2)_n$—CO—where m is an integer of one to five and n is zero or an integer of one to five. The substituent group $R^1$ is selected from the group consisting of hydrogen; alkyl of one to six carbon atoms, optionally substituted with a substituent selected from the group consisting of aminocarbonyl, carboxyl, cyano, halogen, hydroxy, and alkoxy of one to four carbon atoms.

$R^2$ is selected from the group consisting of a) cycloalkyl of three to six carbon atoms; b) cycloalkenyl of five to six carbon atoms; c) phenyl optionally substituted with a substituent selected from the group consisting of alkyl of one to four carbon atoms, alkoxy of one to four carbon atoms, halogen, and hydroxy; d) 1- or 2-naphthyl optionally substituted with a substituent selected from the group consisting of from the group consisting of alkyl of one to four carbon atoms, alkoxy of one to four carbon atoms, halogen, and hydroxy.

$R^3$ and $R^4$ are independently selected from the group consisting of hydrogen, alkyl of one to six carbon atoms, pyridyl; phenyl optionally substituted with a substituent selected from the group consisting of alkyl of one to four carbon atoms, alkoxy of one to four carbon atoms, halogen, and hydroxy; or $R^3$ and $R^4$, taken together represent —$CH_2CH_2OCH_2CH_2$— or —$CH_2CH_2NR^5CH_2CH_2$—where $R^5$ is alkyl of one to four carbon atoms.

A is an aminoacyl residue selected from the group consisting of D-phenylalanyl, D-3-(4-chlorophenyl)alanyl, D-3-(4-fluorophenyl)alanyl, D-3-(quinolin-3-yl)alanyl, sarcosyl, glycyl, azaglycyl, D-3,3-diphenylalanyl, N$^\alpha$-methyl-D-3-(naphth-2-yl)alanyl, and D-3-(naphth-2-yl)alanyl.

B is an aminoacyl residue selected from the group consisting of D-3-(4-chlorophenyl)alanyl, D-3,3-diphenylalanyl, D-3-(4-fluorophenyl)alanyl, D-3-(naphth-2-yl)alanyl, D-phenylalanyl, and D-3-(quinolin-3-yl)alanyl.

C is an aminoacyl residue selected from the group consisting of D-alanyl, D-3-(benzo[b]thien-2-yl)alanyl, glycyl, D-3-(naphth-1-yl)alanyl, D-3-(pyrid-3yl)alanyl, D-3-(quinolin-3-yl)alanyl, and D-3-(thiazol-2-yl)alanyl.

D is an aminoacyl residue selected from the group consisting of glycyl, L-seryl, L-homoseryl, L-seryl(O-benzyl), and N$^\alpha$(R$^1$)-L seryl where R$^1$ is alkyl of from one to four carbon atoms.

E is an aminoacyl residue selected from the group consisting of N$^\alpha$(R$^1$)-alanyl, N$^\alpha$(R$^1$)-(3-(4-(3-amino-1,2,4-triazol-5-yl)amino)phenyl)alanyl, N$^\alpha$(R$^1$)-(3-4-((3-amino-1,2,4-triazol-5-yl)amino)methyl)phenyl)alanyl, N$^\alpha$(R$^1$)-(3-(4-(3-amino-1,2,4-triazol-5-yl)amino)cyclohexyl)alanyl, N$^\alpha$(R$^1$)-(3-(4-(nicotinyl)amino)cyclohexyl)alanyl, N$^\alpha$(R$^1$)-(N-ε-nicotinyl)lysyl, N$^\alpha$(R$^1$)-

(N-ε-(3-amino-1,2,4-triazol-5-yl)lysyl, $N^\alpha(R^1)$-3-(4-nitrophenyl)alanyl, $N^\alpha(R^1)$-3-(4-aminophenyl $N^\alpha(R^1)$-3-(4-aminocyclohexyl)alanyl, $N^\alpha(R^1)$-tyrosyl, $N^\alpha(R^1)$-tyrosyl(O-methyl), $N^\alpha(R^1)$-phenylalanyl, $N^\alpha(R^1)$-cyclohexylalanyl, $N^\alpha(R^1)$-glycyl, $N^\alpha(R^1)$-arginyl, $N^\alpha(R^1)$-histidyl, and $N^\alpha(R^1)$-homoarginyl; where $R^1$ is hydrogen or alkyl of from one to four carbon atoms.

F is an aminoacyl residue selected from the group consisting of glycyl, icitrullyl, D-omocitrullyl, β-alanyl, and an aminoacyl residue of the structure

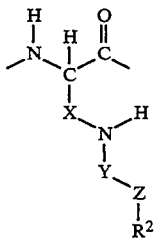

where X is selected from the group consisting of —$(CH_2)_n$—where n is one to six and

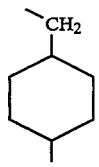

Y is absent or is an aminoacyl residue selected from the group consisting of D-alanyl, L-alanyl, 4-aminobutyryl, 5-aminopentanoyl, 6-aminohexanoyl, 7-aminoheptanoyl, 8-amino-octanoyl, 11-aminoundecanoyl, azaglycyl, D-3-(benzo[b]thien-2-yl)alanyl, L-3-(benzo[b]thien-2-yl)alanyl, D-3-(4-chlorophenyl)alanyl, D-cyclohexylanalyl, glycyl, D-histidyl, D-histidyl(benzyl), D-leucyl, D-3-(naphth-2-yl)alanyl, D-phenylalanyl, D-3-(pyrid-3-yl)alanyl, sarcosyl, seryl, D-seryl, D-threonyl, D-3-(thiazol-4-yl)alanyl, D-tryptyl, D-tyrosyl, D-tryosyl(O-methyl), and D-valyl.

Z is either absent or is an aminoacyl residue selected from the group consisting of D-alanyl, L-alanyl, azaglycyl, D-cyclohexylalanyl, glycyl, D-histidyl, D-phenylalanyl, 3-((4-(3-amino- 1,2,4-triazol-5-yl)amino)-phenyl)alanyl, (3-(4-((3-amino-1,2,4-triazol-5-yl)amino)-methyl)phenyl)alanyl, sarcosyl, D-seryl, L-seryl, and

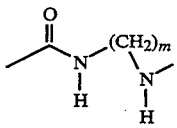

where m is an integer of from one to twelve, inclusive.

$R^2$ is 3-amino-1,2,4-triazol-5-yl or is an acyl group selected from the group consisting of acetyl; (4-acetylpiperazin-1-yl)carbonyl; (adamant-1-yl)carbonyl; benzoyl, optionally substituted with a group selected from alkyl of one to four carbon atoms, alkoxy of one to four carbon atoms, and halogen; butyryl; cycolhexylcarbonyl; dihydroshikimyl; formyl; nicotinyl; 2-furoyl; 2- and 6-hydroxynicotinyl; (indol-2-yl)carbonyl; isonicotinyl; (4-methylpiperazin-1-yl)carbonyl; (morphilin-1-yl)carbonyl; 2- and 6-methylnicotinyl; 1- and 2-naphthoyl optionally substituted with a group selected from alkyl of one to four carbon atoms, alkoxy of one to four carbon atoms, and halogen; picolyl; (piperazin-1-yl)carbonyl; propionyl, pyrazinoyl; pyridylacetyl; (pyrrolyl)carbonyl; (3- or 4-quinolinyl)carbonyl; salicyl; shikimyl; 2-(tetrahydrofuroyl), and (thien-2-yl)carbonyl.

G is an aminoacyl residue selected from the group consisting of L-leucyl; $N(R^1)$-L-leucyl; glycyl; sarcosyl; prolyl; L-valyl; L-cyclohexylalanyl; and $N^\alpha(R^1)$-L-cyclohexylalanyl; where $R^1$ is hydrogen or alkyl of from one to six carbon atoms.

H is an an-finoacyl residue selected from the group consisting of L-citrullyl; L-homocitrullyl; L-histidyl; L-(N-ε-isopropyl)lysyl; L-arginyl; and $N^\alpha(R^1)$-L-arginyl; L-homoarginyl; L-2-amino-6-$N^g$-ethylguanidinohexanoyl; and L-2-amino-6-$N^gN^g$-diethylguanidinohexanoyl.

I is an aminoacyl residue selected from the group consisting of L-prolyl; 4-hydroxy-L-prolyl; L-pipecolyl; L-azetidinyl; L-2,8-tetrahydroisoquinoline-2-carbonyl, $N(R^1)$-L-leucyl; sarcosyl; glycyl; and $N(R^1)$-L-alanyl; where $R^1$ is hydrogen or alkyl of from one to six carbon atoms.

J is —$NH(CH_2CH_3)$ or is an aminoacyl residue selected from the group consisting of D-alanylamide, D-alanyl(OH), D-glutamyl(OH), L-glutamyl(OH), $N(R^1)$-L-alanylamide, $N(R^1)$-D-alanylamide, sarcosamide, D-serylamide, and azaglycylamide, glycylamide, where $R^1$ is as defined above and with the proviso that when J is —$NH(CH_2CH_3)$ then I is L-prolyl.

In another embodiment of the present invention there are provided pharmaceutical formulations for use in suppressing levels of sex hormones in a mammal comprising a sex hormone suppressing effective amount of a compound as defined above in combination with a pharmaceutically acceptable carrier.

In yet another embodiment of the present invention there is provided a method of suppressing levels of sex hormones in a marrunal comprising administering to a mammal in need of such treatment a therapeutically effective amount of a compound as defined above.

DETAILED DESCRIPTION

As used throughout this specification and the amended claims, the terms "halogen" and "halide" as used herein refers to bromo (Br), chloro (Cl), fluoro (F) or iodo (I).

The terms "resin" or "peptide resin" as used herein refer to resins of the type so commonly used in the art of synthetic peptide preparation. Examples of such resins include, but are not limited to, methyl benzhydrylamine (MBHA) or benzhydrylamine (BHA).

The term "alkyl" as used herein refers to divalent straight or branched group derived from a saturated hydrocarbon by the removal of a single hydrogen atom. Examples of alkyl include, but are not limited to methyl, ethyl, propyl, iso-propyl, butyl, sec-butyl, iso-butyl, tert-butyl, pentyl, hexyl, and the like.

The term "alkylene" refers to a straight or branched divalent group derived from a saturated hydrocarbon by the removal of two hydrogen atoms. Examples of alkylene include —$CH_2$—, —$CH_2CH_2$—, —$CH(CH_3)CH_2$—and the like.

The term "azetidinyl" refers to the cyclic aminoacyl residue derived from azetidine-2-carboxylic acid.

The term "cycloalkyl" refers to a monovalent cyclic hydrocarbon group derived from a cyclic saturated hydrocarbon group by the removal of a single hydrogen atom. Examples of cycloalkyl groups include cyclopropyl, cycobutyl, cyclohexyl, cycloheptyl, bicyclo[2.2.2]octane, and the like.

The term "cycloalkenyl" refers to a monovalent group derived by removal of a single hydrogen atom from a cyclic hydrocarbon molecule which contains a carbon-carbon double bond, while "cycloalkylene" refers to a divalent group derived from a saturated cyclic hydrocarbon by the removal to two hydrogens. Examples of cycloalkenyl groups include cyclopent-2-en-1-yl, cyclohex-1-enyl, and the like while is examples of cycloalkylene groups include cyclopentylene, cycohexylene, and the like.

The term "succinamyl" denotes the group $H_2N(CO)CH_2CH_2CO-$.

Unless indicated otherwise by a "D" prefix, the stereochemistry of the alphacarbon atom of the amino acids and aminoacyl residues in peptides described in this specification and the appended claims is the natural or "L" configuration. The Cahno Ingold-Prelog "R" and "S" designations are used to specify the stereochemistry of chiral centers in certain of the acyl substituents at the N-terminus of the peptides of this invention. The designation "R,S" is meant to indicate a racemic mixture of the two enantiomeric forms. This nomenclature follows that described in R. S. Cahn, C. K. Ingold, and V. Prelog, *Angew, Chem., Int. Ed. Engl.*, 5:385–415 (1966).

For the most part, the names of naturally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)," *Biochemistry*, 14(2):1975). To the extent that the names and abbreviations of amino acids and aminoacyl residues employed in this specification and appended claims differ from those suggestions, they will be made clear to the reader by the following.

"Atz" or "Atza" means the substituent group 3-amino-1,2,4-triazol-5-yl. "Bal" stands for 3-(benzo[b]-thien-2-yl)alanine, with "Thial" and "Thiaz" representing 3-(thien-2-yl) alanine and 3-(thiazolyl)alanine, respectively.

"Cha" represents 3-cyclohexylalanine and various amino acids derived from phenylalanine by substitution of the phenyl group are represented by abbreviations such as "D4ClPhe," "D4FPhe," "D4NO2Phe," and "D4NH2Phe" which represent D-3-(4-chlorophenyl) alanine, D-3-(4-fluorophenyl)alanine, D-3-(4-nitrophenyl)alanine, s and D-3-(4-aminophenyl)alanine, respectively.

"Cit" and "HCit" stand for citrullyl and homocitrullyl (or L-2-amino-(6-aminocarbonylanfino)hexanoic acid), respectively.

"DLys(Nic)" or "D-Lys(N-epsilon nicotinyl)" represents a D-lysine amino acid or aminoacyl residue substituted on the epsilon nitrogen atom of the side chain by a nicotinyl acyl group. Similarly, "DLys(Isonic)," "DLys(Shik)," "DLys(Fur)," and "DLys(THF)" represent D-lysine acylated on the epsilon nitrogen atom by an isonicotinyl, shikimyl, fur-2-oyl, or tetrahydrofur-2-oyl group. "DLys(Isp)," "DLys(Nisp)" or "D-Lys(N-epsilon isopropyl)" stand for a lysine substituted on the epsilon amino group of the lysine side-chain by an isopropyl group.

"Harg" stands for homoarginyl or L-2-amino-6-guanidinohexanoyl). "HargEt" and "HargEt$_2$" represent L-2-amino-6-N$^g$-ethylguanidinohexanoic acid and L-2-amino-6-N$^g$,N$^g$-diethylguanidinohexanoic acid, respectively.

"D1Nal" and "D2Nal" represent D-3-(naphth-1-yl)alanine and D-3-(naphth-2-yl)alanine, respectively. "D3Pal" represents D-3-(pyrid-3-yl)alanine and "D3Qal" or "D3Qual" stands for D-3-(quinol-3-yl)alanine. "D-(4-Atza)Phe" or "DAtzPhe" means D-3-(4-(3-amino-1H-1,2,4-triazol-5-yl)amino)phenyl)alanine and "D-(4-Atzame)Phe" or "D-(AtzMePhe)" represents D-3-(4-(((3-amino-1H- 1,2,4'-triazol-5-yl)amino)methyl)phenyl)alanine.

"Sar" and "SarNH$_2$" mean sarcosine or the antide of sarcosine, respectively.

By the term "pharmaceutically acceptable salt" is meant salts recognized in the pharmaceutical formulation arts as non-toxic and suitable for use in formulations intended for use in human and animal treatment. Suitable acids and bases useful for this purpose are listed, for example, in the review article, "Pharmaceutical Salts" by S. N. Berge, etal., *J. Pharm. Sci.*, 66:1–19 (1977).

Representative examples of compounds contemplated as falling within the scope of the present invention include, but are not limited to the following:

N-Isobutyryl-D2Nal- D4ClPhe-D3Pal-Ser-NMeTyr-DLys(N-epsilon-Nicotinyl)-Leu-Lys(N-epsilon-Isopropyl)-Pro-DAlaNH$_2$;

N-Methoxyacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Cyclopropylcarbonyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Cyclopentylcarbonyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Cyclohexylcarbonyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Cyclohexylacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-Benzoyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$:

N-Phenylacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$;

N-3-Phenylpropionyl-D2Nal-D4ClPhe-D3Pal-Ser-NMeTyr-DLys(N-epsilon-Nicotinyl)-Leu-Lys(N-epsilon-Isopropyl)-Pro-DAlaNH $_2$;

N-3-(4-Hydroxyphenyl)propionyl-D2Nal-D4ClPhe-D3Pal-Ser-NMeTyr-DLys(N-epsilon-Nicotinyl)-Leu-Lys(N-epsilon -Isopropyl)-Pro-D AlaNH$_2$;

N-2-(4-Fluorophenyl)propionyl-D2Nal-D4ClPhe-D3Pal-Ser-NMeTyr-DLys(N-epsilon-Nicotinyl)-Leu-Lys(N-epsilon -Isopropyl)-Pro-D AlaNH$_2$;

N-3-(2-Naphthyl)propionyl-D2Nal-D4ClPhe-D3Pal-Ser-NMeTyr-DLys(N-epsilon-Nicotinyl)-Leu-Lys(N-epsilon-Isopropyl )-Pro-DAlaNH$_2$;

N-Succinyl-D2Nal-D4ClPhe-D3Pal-Ser-NMeTyr-DLys(Nicotinyl)-Leu-Lys(N-epsilon-Isopropyl)-Pro-DAlaNH$_2$;

N-Cyclopropylcarbonyl-D2Nal-D4ClPhe-D3Pal-Ser-NMeTyr-DCit-Leu-Arg-Pro-DAlaNH$_2$;

N-Phenyl acetyl-D2Nal-D4ClPhe-D3Pal-Ser-NMeTyr-DCit-Leu-Arg-ProDAlaNH2;

N-Succinyl-D2Nal-D4ClPhe-D3Pal-Ser-NMeTyr-DCit-Leu-Arg-Pro-DAlaNH2;

N-(Aminocarbonyl)-D2Nal-D4ClPhe-D3Pal-Ser-NMeTyr-DCit-Leu-Arg-ProDAlaNH2;

N-(Ethylaminocarbonyl)-D2Nal-D4ClPhe-D3Pal-Ser-NMeTyr-DCit-Leu-Arg-Pro-DAlaNH2;

N-(Morpholinocarbonyl)-D2Nal-D4ClPhe-D3Pal-Ser-NMeTyr-DCit-Leu-Arg-Pro-DAlaNH2;

N-(Morpholinoethylaminocarbonyl)-D2Nal-D4ClPhe-D3Pal-Ser-NMeTyr-DCit-Leu-Arg-Pro-DAlaNH2;

N-(N'-Methylpiperazinylcarbonyl)-D2Nal-D4ClPhe-D3Pal-Ser-NMeTyr-DCit-Leu-Arg-Pro-DAlaNH2;

N-(2-Pyridylmethylaminocarbonyl)-D2Nal-D4ClPhe-D3Pal-Ser-NMeTyr-DCit-Leu-Arg-Pro-DAlaNH2;

N-(3-Pyridylmethylaminocarbonyl)-D2Nal-D4ClPhe-D3Pal-Ser-NMeTyr-DCit-Leu-Arg-Pro-DAlaNH2; and N-(2-Pyridylethylaminocarbonyl)-D2Nal-D4ClPhe-D3PaloSer-NMeTyr-DCit-Leu-Arg-Pro-DAlaNH2.

Preferred compounds of the present invention have the structure

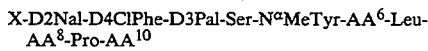

X-D2Nal-D4ClPhe-D3Pal-Ser-N$^\alpha$MeTyr-AA$^6$-Leu-AA$^8$-Pro-AA$^{10}$ where X is as defined above.

AA$^6$ is an aminoacyl residue selected from the group consisting of D-citrullyl, D-lysyl(N-epsilon nicotinyl), D-lysyl(N-epsilon glycyl nicotinyl), D-lysyl(N-epsilon azaglycyl nicotinyl), D-lysyl(N-epsilon shikimyl), D-lysyl(N-epsilon glycyl shikimyl), D-lysyl(N-epsilon azaglycyl shikimyl), D-lysyl(N-epsilon dihydroshikimyl), D-lysyl(N-epsilon glycyl dihydroshikimyl), D-lysyl(N-epsilon azaglycyl dihydroshikimyl), D-lysyl(N-epsilon fur-2-oyl), D-lysyl(N-epsilon glycyl fur-2-oyl), D-lysyl(N-epsilon azaglycyl fur-2-oyl), D-lysyl(N-epsilon tetrahydrofur-2oyl), D-lysyl(N-epsilon glycyl tetrahydrofur-2-oyl), and D-lysyl(N-epsilon azaglycyl tetrahydrofur-2-oyl).

AA$^8$ is an aminoacyl residue selected from the group consisting of L-arginyl, L-homoarginyl, L-lysyl(N-ε-isopropyl), L-2-amino-6-(N$^g$,N$^g$-diethylguanidino)hexanoyl, L-citrullyl, L-homocitrullyl, and L-histidyl.

AA$^{10}$ is an aminoacyl residue selected from the group consisting of D-alanylamide, and D-sarcosamide.

Examples of compounds of this type include:
N-Glycolyl-D2Nal-D4ClPhe-D3Pal-Ser-NMeTyr-DCit-Leu-Arg-Pro-DAlaNH2;

N-Formyl-D2Nal-D4ClPhe-D3Pal-Ser-NMeTyr-DCit-Leu-Arg-Pro-DAlaNH2;

N-Propionyl-D2Nal-D4ClPhe-D3Pal-Ser-NMeTyr-DCit-Leu-Arg-Pro-DAlaNH2;

N-Butyryl-D2Nal-D4ClPhe-D3Pal-Ser-NMeTyr-DCit-Leu-Arg-Pro-DAlaNH2;

N-Succinamyl-D2Nal-D4ClPhe-D3Pal-Ser-NMeTyr-DCit-Leu-Arg-ProDAlaNH2;

N-Formyl-D2Nal-D4ClPhe-D3Pal-Ser-NMeTyr-DLys(Nicotinyl)-Leu-Lys(N-epsilon-Isopropyl)-Pro-DAlaNH2;

N-Propionyl-D2Nal-D4ClPhe-D3Pal-Ser-NMeTyr-DLys(N-epsilon-Nicotinyl)-Leu-Lys(N-epsilon-Isopropyl)-Pro-DAlaNH2;

N-Butyryl-D2Nal-D4ClPhe-D3Pal-Ser-NMeTyr-DLys(N-epsilon-Nicotinyl)-Leu-Lys(N-epsilon-Isopropyl)-Pro-DAlaNH2; and N-Cyanoacetyl-D2Nal-D4ClPhe-D3Pal-Ser-NMeTyr-DLys(N-epsilon-Nicotinyl)-Leu-Lys(N-epsilon-Isopropyl)-Pro-DAlaNH2.

LHRH Antagonist Activity

Representative compounds of the present invention were evaluated in an in vitro test for LHRH antagonist potency (pA$_2$). The test employed the method detailed in F. Haviv, et al. *J. Med. Chem.*, 32:2340–2344 (1989). The values of pA$_2$ are the negative logarithms of the concentration of the particular antagonist test compound required to shift the response curve produced by the agonist leuprolide to two-fold higher concentration. (Leuprolide is the LHRH agonist having the structure 5-oxo-Pro$^1$-His$^2$-Trp$^3$-Ser$^4$-Tyr$^5$ -D-Leu$^6$-Leu$^7$-Arg$^8$-Pro$^9$-NHEt and is disclosed and claimed in U.S. Pat. No. 4,005,063.) Typically pA$_2$ values of 9.5 or greater are indicative of good LHRH antagonist potency, with values of 10.0 or greater being preferred.

The results of these tests for representative compounds in accordance with this invention are presented in Table 1.

TABLE 1

| Example No. | pA$_2$ | Example No. | pA$_2$ |
|---|---|---|---|
| 1 | 11.8 | 4 | 11.18 |
| 2a | 11.3 | 5a | 11.35 |
| 2b | 11.05 | 5b | 11.46 |
| 2c | 10.75 | 5c | 11.25 |
| 2d | 11.14 | 5d | 11.19 |
| 2e | 11.5 | 5e | 10.95 |
| 2f | 11.45 | 5f | 10.8 |
| 2g | 10.15 | 6 | 10.4 |
| 2h | 9.95 | 7 | 11.22 |
| 2i | 8.8 | 8a | 10.03 |
| 2j | 10.3 | 8b | 10.7 |
| 2k | 10.85 | 8c | 10.31 |
| 2l | 10.9 | 8d | 10.4 |
| 2m | 10.7 | 8e | 11.17 |
| 2n | 10.16 | 8f | 10.44 |
| 2o | 10.1 | 8g | 10.75 |
| 3 | 10.29 | | |

The compounds of the present invention act as LHRH antagonists and are useful for suppressing levels of gonadotropins and androgens in mammals.

In the practice of the method of this invention an amount of a compound of the invention or a pharmaceutical composition containing the antagonists, effective to suppress levels of sex hormones in a mammal, is administered to the host in need of such treatment. These compounds or compositions may be administered by any of a variety of routes depending upon the specific end use, including orally, parenterally (including subcutaneous, intramnuscular and intraveneous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 0.01 and 10 mg/kg body weight per day, preferably between about 0.1 and 5.0 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be so prepared for use for parenteral (subcutaneous, intramuscular or intravenous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like.

Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturofic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, nonantigenic polymer such as a polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

Synthesis of the Compounds of the Invention

In general, the compounds of the present invention are synthesized by techniques known to those skilled in the art as, for example, by so-called "solid phase" peptide synthesis or by usual methods of solution phase chemistry. A summary of available solid phase peptide synthetic techniques may be found in J. M. Stewart and J. D. Young, *Solid Phase Peptide Synthesis*, W. H. Freeman Co., San Francisco, 1963 and J. Meienhofer, *Hormonal Proteins and Peptides*, Vol. 2., p.46, Academic Press (New York), 1973. For classical solution synthesis see G. Schroder and K. Lupke, *The Peptides*, vol. 1, Academic Press (New York), 1965.

In general, these methods comprise the sequential addition of one or more an-fino acids or suitably protected amino acids to a growing peptide chain bound to a suitable resin. The starting amino acids are commercially available or, where novel in the compounds of this invention, are synthesized by methods detailed below from readily available starting materials.

Normally, either the antino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conducive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing peptides involves solid phase peptide synthesis. In this method of preparing peptides, the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5-dimethoxybenzyloxycarbonyl, o-nitrophenylsulfenyl, 2-cyano-t-butyloxycarbonyl, 9-fluorenyhnethyloxycarbonyl and the like. The t-butyloxycarbonyl ("BOC" or "t-BOC") protecting group is preferred.

Particularly preferred side chain protecting groups are, for side-chain amino s groups as in lysine and arginine: nitro, p-toluene-sulfonyl, 4-methoxybenzenesulfonyl, Cbz, BOC and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl and tetrahydropyranyl; for histidine: benzyl, Cbz, p-toluenesulfonyl and 2,4-dinitrophenyl; for tryptophan: formyl.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are chloromethylpolystyrenedivinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylaminopolystyrene-divinylbenzene polymer described by P. Rivaille, et al, *Helv. Chim. Acta.*, 54, 2772 (1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40 and 60° C., for from about 12 to 48 hours. Preferred reagents and reaction conditions involve the coupling of an alpha-N-BOC amino acid cesium salt with the resin in DMF at about 50° C. for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBt), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours, preferably about 12 hours at a temperature of between about 10° and 50° C., most preferably 25° C. in a solvent such as dichloromethane or DMF, preferably dichloromethane. The coupling of the carboxyl group to the N-methyl-Ser(OBzl) attached to the peptide resin requires catalysis by 4-dimethylaminopyridine (DMAP), in addition to the carbodiimide reagent.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

The side-chain modifications of the peptides of the present invention are carried out by methods detailed below in Preparations A–B.

Preparation A

N-(t-Butoxycarbonyl)-N-Methyl-(4-FMOC-aminomethyl)Phenylalanine

A mixture of N-trifluoroacetyl-N-methyl-phenylalanine (1 equivalent) and zinc chloride (0.9 to 2.2 equivalents) in chloromethylether is heated at 65° C. for 10–24 hr. The excess reagent is removed in vacuo and the residue is dissolved in $CH_2Cl_2$, washed with saturated $NaHCO_3$ solution, then with saturated sodium chloride solution. The organic phase is dried ($Na_2SO_4$) and concentrated. The crude product is purified by column chromatography to yield the N-methyl-4-(chloromethyl)phenylalanine methyl ester. This is treated with aqueous hydrochloric acid to cleave the methyl ester. The N-methyl-(4-chloromethyl)phenylalanine hydrochloride is o treated with di-t-butylcarbonate (1.2 equivalents) in the presence of triethylamine (1 equivalent) in THF at 0° C. for 1 hr. After work-up and purification BOC-N-methyl-(4-chloromethyl)phenylalanine is obtained.

BOC-N-Me-(4-chloromethyl)phenylalanine is heated under reflux for 4 to 24 hr with excess of sodium azide and catalytic amount of sodium iodide in methanol. The residue is treated with dilute hydrochloric acid to pH 6 and extracted with ethyl acetate. The organic extracts are dried and concentrated to yield BOC-N-methyl-(4-azidomethyl)phenylalanine.

This is hydrogenated over Pd/C catalyst in methanol to afford BOC-N-methyl-(4-aminomethyl)phenylalanine. The last compound is treated with 9-fluorenylmethyl chlorocarbonate under basic conditions as described in page 24 of "The Practice of Peptide Synthesis" by M. Bodanszky and A. Bodanszky. After work-up and purification N-(t-butoxycarbonyl)-N-methyl-(4-FMOC-aminomethyl)phenylalanine is obtained (see Scheme 1).

Scheme 1

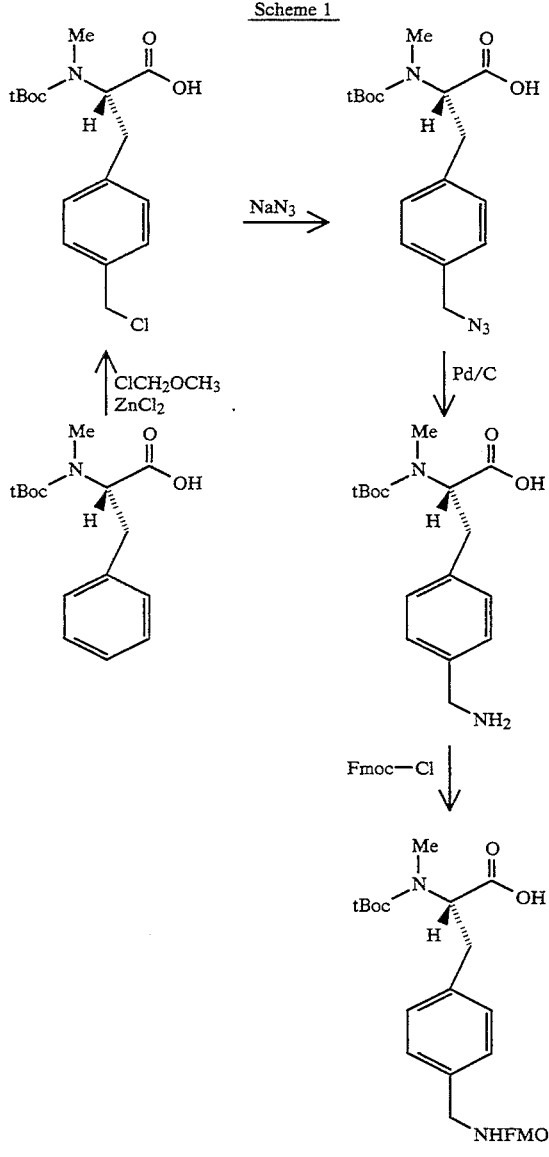

Preparation B
N-(t-Butoxycarbonyl)-D-(4-FMOC-aminomethyl)-Phenylalanine

BOC-D-(4-chloromethyl)phenylalanine is synthesized according to Preparation A described above. The product is first treated with sodium azide in methanol, using analogous conditions to those previously described, and then hydrogenated to yield N-BOC-D-(4-aminomethyl)phenylalanine which is substituted with FMOC, as previously described, to afford N-(t-Butoxycarbonyl)-D-(4-FMOC-aminomethyl)Phenylalanine.

The Atz or 3-amino-1,2,4-triazol-5-yl group can be attached to the 4-amino group of 3-(4-aminophenyl)alanine or the terminal amino group the omega-aminoalkyl side chain of any alpha,omega-diaminocarboxylic acid amino acid by the method detailed below in Scheme 2 which illustrates the process for $N^\alpha$-methyl-3-(4-aminophenyl)alanine.

As shown in Scheme 2 below, upon the completion of the synthesis of a peptide-resin containing an $N^\alpha$-methyl-3-(4-aminophenyl)alanine residue, the peptide resin is treated with 30% piperidine/DMF for 2 to 24 hr, to cleave the FMOC group from the N-4-amino position of the N-Me-Phe residue. The peptide-resin is washed, 3 times with methylene chloride, 3 times with DMF, and reacted with 10- to 20-fold excess of diphenylcyanocarboimidate in DMF overnight (see Scheme 2 below), washed, 3 times with methylene chloride, 3 times with DMF, and then reacted with 20- to 100fold excess of hydrazine in DMF overnight. The peptide-resin is washed, as previously described, dried over $P_2O_5$ overnight, and treated with HF/anisole as above.

SCHEME 2

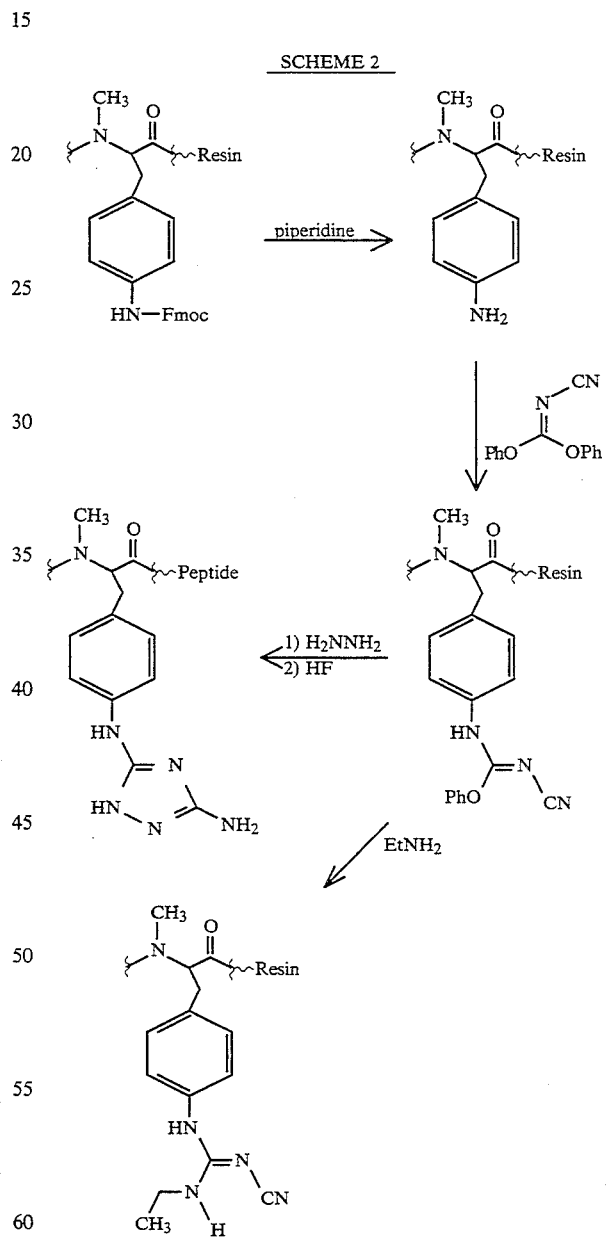

The process of Scheme 2 above is similarly used for the attachment of the Atz group to, for example, the epsilon-amino group in the side chain of lysine or similar aminoacyl residue having an omega-aminoalkyl side chain group.

Example 1

N-Formyl-D2Nal-D4ClPhe-D3Pal-Ser-NMeTyr-DLys(Nicotinyl)-Leu-Lys(N-epsilon-Isopropyl)-Pro-DAlaNH$_2$ (1b)

In the reaction vessel of a Milligen-Biosearch 9500 peptide synthesizer was placed 1 g (0.6 mmol) of-D-Ala-NH-resin (4-methyl-benzhydrylamine resin). Amino acids were added sequentially according to the following synthetic cycle:

1. Deblocking, to remove the t-BOC group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution for one minute and then the deblocking reaction is run for 20 minutes.
2. Base wash, to remove and neutralize the TFA used for deprotection, is carried out using a solution of 10% N,N'-diisopropylethylamine in methylene chloride. The resin is washed with base three times for one minute each time after a deblocking step.
3. Coupling reaction is carried out using a 3-fold molar excess of 0.3 M DMF solution of a t-BOC protected amino acid derivative along with a 3-fold molar excess of 0.3 M methylene chloride solution of diisopropylcarbodimide as activator. The activated amino acid is then coupled to the free alpha amino group of the peptide-esin. The reaction time is as described in the synthesis protocol.
4. Wash, each reaction step is followed by three washes of one minute each: one of methylene chloride, one of (1:1) methylene chloride/DMF, and one of DMF.

Synthesis Protocol

The amino protected amino acids are coupled to the resin according the following order, number, and duration of couplings:

| # | Amino Acid | Coupling |
|---|---|---|
| 1. | BOC—Pro | two-1h |
| 2. | BOC—Lys(N-epsilon-Cbz, Isopropyl) | two-1h |
| 3. | BOC—Leu | two-1h |
| 4. | BOC—D—Lys(N-epsilon-Nicotinyl) | two-1h |
| 5. | BOC—NMe—Tyr(O-2,6-diCl—Bzl) | two-1h |
| 6. | BOC—Ser(OBzl) | two-1h |
| 7. | BOC—D-3Pal | two-6h |
| 8. | BOC—D-4ClPhe | two-2h |
| 9. | BOC—D2Nal | two-2h |
| 10. | formic acid | two-2h |

Upon completion of the synthesis the resin is dried overnight over P$_2$O$_5$ under vacuum and then treated with dry HF in the presence of anisole at 0° C. for 1 h to cleave the peptide from the resin. The excess of reagent is removed in vacuo. The resin is washed first with ether, then stirred at room temperature with a solution of (1:1:0.1) water/acetonitrile/acetic acid (50 ml) for 15 minutes, and filtered. The filtrate is lyophilized to give the crude peptide as a fluffy powder. This is purified by HPLC using a (25×2.5 cm) Dynamax C-18 column (8 micron) with solvent is mixtures varying in a gradient ranging from 89% H$_2$O/11% CH$_3$CN/0.1% TFA over a period of 20 minutes. The UV detector is set at 260 nm. The product is eluted at 25.95 min as a single peak, collected and lyophilized to give pure NFormyl-D2NalD-4ClPhe-D3Pal-Ser-NMeTyr-DLys(N-epsilon-Nicotinyl)-Leu-Lys(N-epsilon-Isopropyl)-Pro-DAlaNH$_2$ (1b) as the trifluoroacetate salt; FAB Mass spec. m/e 1520 (M+H)$^+$. Amino Acid Anal: 0.98 Ala; 1.02 Pro; 1.67 Lys; 1.00 Leu; 1.18 NMeTyr.

Example 2

The procedure described in Example 1 was used but substituting the appropriate acids for formic acid. After work-up, lyophilization, and HPLC purification the following compounds were obtained:

Example 2a

N-Propionyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (2b) is obtained as the trifluoroacetate salt; R$_t$=26.86 min; FAB Mass spec. m/e 1549 (M+H)$^+$. Amino Acid Analysis: 0.98 Ala;. 1.02 Pro; 1.01 Leu; 1.59 Lys; 0.86 NMeTyr; 0.53 Ser.

Example 2b

N-Butyryl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (3b) is obtained as the trifluoroacetate salt; R$_t$=29.91 min: FAB Mass spec. m/e 1563 (M+H)$^+$. Amino Acid Analysis: 0.98 Ala;. 1.01 Pro; 1.01 Leu; 1.66 Lys; 1.16 NMeTyr; 0.49 Ser.

Example 2c

N-Isobutyryl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (4b) is obtained as the trifluoroacetate salt; R$_t$=20.00 min: FAB Mass spec. m/e 1562 (M+H)$^+$. Amino Acid Analysis: 1.03 Ala; .0.99 Pro: 0.99 Lys(Isp); 0.98 Leu;. 1.00 Lys; 0.93 NMeTyr; 0.46 Ser; 0.98 D3Pal; 0.99 D4ClPhe.

Example 2d

N-Methoxyacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (Sb) is obtained as the trifluoroacetate salt; R$_t$=26.30 min; FAB Mass spec. m/e 1564 (M+H)$^+$. Amino Acid Analysis: 0.99 Ala; .0.99 Pro; 1.06 Lys(Isp); 1.02 Leu; 0.99 Lys; 0.81 NMeTyr; 0.53 Ser; 1.04 D3Pal; 1.11 D4ClPhe.

Example 2e

N-Cyanoacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (6b) is obtained as the trifluoroacetate salt; R$_t$=26.96 min; FAB Mass spec. m/e 1559 (M+H)$^+$. Amino Acid Analysis: 0.99 Ala; .1.02 Pro; 0.96 Lys(Isp); 1.02 Leu; 0.97 Lys; 1.00 NMeTyr; 0.49 Ser; 1.02 D3Pal; 1.04 D4ClPhe.

Example 2f

N-Cyclopropylcarbonyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (8b) is obtained as the trifluoroacetate salt: R$_t$=28.75 min; FAB Mass spec. m/e 1560 (M+H)$^+$. Amino Acid Analysis: 0.97 Ala;. 1.03 Pro; 1.01 Leu; 1.66 Lys; 1.18 NMeTyr; 0.49 Ser.

Example 2g

N-Cyclopentylcarbonyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (9b) is obtained as the trifluoroacetate salt; R$_t$=32.75 min; FAB Mass spec. m/e 1588 (M+H)$^+$. Amino Acid Analysis: 1.0

Ala;. 1.01 Pro; 0.97 Lys(Isp); 1.01 Leu; 0.99 Lys; 0.97 NMeTyr; 0.52 Ser; 0.93 D3Pal; 0.95 D4ClPhe.

Example 2h

N-Cyclohexylcarbonyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (10b) is obtained as the trifluoroacetate salt; R$_t$=33.70 min; FAB Mass spec. m/e 1600 (M+H)$^+$. Amino Acid Analysis: 1.03 Ala; .0.98 Pro; 0.90 Lys(Isp); 0.98 Leu; 1.00 Lys; 0.78 NMeTyr; 0.49 Ser; 0.75 D3Pal; 0.77 D4ClPhe.

Example 2i

N-Cyclohexylacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (1b) is obtained as the trifluoroacetate salt; R$_t$=36.33 min; FAB Mass spec. m/e 1616 (M+H)$^+$. Amino Acid Analysis: 1.00 Ala; .0.99 Pro; 0.98 Lys(Isp); 1.00 Leu; 1.00 Lys; 1.00 NMeTyr; 0.57 Ser; 0.90 D3Pal; 0.89 D4ClPhe.

Example 2j

N-Benzoyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (25b) is obtained as the trifluoroacetate salt; R$_t$=31.95 min; FAB Mass spec. m/e 1596 (M+H)$^+$. Amino Acid Analysis: 0.99 Ala; .1.01 Pro; 0.97 Lys(Isp); 1.03 Leu; 0.97 Lys; 1.00 NMeTyr; 0.48 Ser; 1.02 D3Pal; 1.12 D4ClPhe.

Example 2k

N-Phenylacetyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (26b) is obtained as the trifluoroacetate salt; R$_t$=32.11 min: FAB Mass spec. m/e 16 11 (M+H)$^+$. Amino Acid Analysis: 0.98 Ala;. 1.02 Pro;1.01 Leu; 1.60 Lys; 0.87 NMeTyr; 0.54 Ser.

Example 2l

N-3-Phenylpropionyl-D2Nal-D4ClPhe-D3Pal-Ser-NMeTyr-DLys(N-epsilon-Nicotinyl)-Leu-Lys(N-epsilon-Isopropyl)-Pro-DAlaNH$_2$ (27b) is obtained as the trifluoroacetate salt; R$_t$=33.18 min; FAB Mass spec. m/e 1625 (M+H)$^+$. Amino Acid Analysis: 0.98 Ala; .1.01 Pro;1.01 Leu; 1.61 Lys; 0.80 NMeTyr; 0.54 Ser.

Example 2m

N-3-(4-Hydroxyphenyl)propionyl-D2Nal-D4ClPhe-D3Pal-Ser-NMeTyr-DLys(N-epsilon-Nicotinyl)-Leu-Lys(N-epsilon -Isopropyl)-Pro-DAlaNH$_2$ (28b) is obtained as the trifluoroacetate salt; R$_t$=41.90 min; FAB Mass spec. m/e 1640 (M+H)$^+$. Amino Acid Analysis :0.98 Ala;. 1.01 Pro; 1.01 Leu; 1.61 Lys; 0.80 NMeTyr; 0.54 Ser.

Example 2n

N-2-(4-Fluorophenyl)propionyl-D2Nal-D4ClPhe-D3Pal-Ser-NMeTyr-DLys(N-epsilon-Nicotinyl)-Leu-Lys(N-epsilon -Isopropyl)-Pro-DAlaNH$_2$ (29b) is obtained as the trifluoroacetate salt; R$_t$=35.03 min; FAB Mass spec. m/e 1642 (M+H)$^+$. Amino Acid Analysis :0.98 Ala; .1.02 Pro; 0.99 Leu; 1.66 Lys; 1.10 NMeTyr; 0.50 Ser.

Example 2o

N-3(2-Naphthyl)propionyl-D2Nal-D4ClPhe-D3Pal-Ser-NMeTyr-DLys(N-epsilon-Nicotinyl)-Leu-Lys(N-epsilon-Isopropyl) -Pro-DAlaNH$_2$ (30b) is obtained as the trifluoroacetate salt; R$_t$=38.60 min; FAB Mass spec. m/e 1675 (M+H)$^+$. Amino Acid Analysis: 1.02 Ala; .0.98 Pro; 1.03 Leu; 0.97 Lys; 0.90 NMeTyr; 0.55 Ser; 0.94 D3Pal; 0.91 D4ClPhe.

Example 3

N-Succinyl-D2Nal-D4ClPhe-D3Pal-Ser-NMeTyr-DLys(Nicotinyl)-Leu-Lys(N-epsilon-lsopropyl.)-Pro-DAlaNH$_2$(7b)

The procedure described in Example 1 was used to prepare the peptide-resin BOC-D2Nal-D4ClPhe-D 3Pal-Ser(OBzl)-NMeTyr(O-2,6Cl-Bzl)-DLys(N-epsilon-Nicotinyl)-Leu-Lys(N-epsilon-Isopropyl,Cbz) -Pro-DAlaNH-resin. The N-terminus of the peptide was deprotected using the standard deblock procedure. After a two base washes and three (1:1) DMF/DCM washes the resin was treated with excess of succinic anhydride in DMF overnight. After HF treatment, work-up, lyophilization, and HPLC purification NSuccinyl-D2Nal-D4ClPhe-D3Pal-Ser-NMeTyr-DLys(-Nicotinyl)-Leu-Lys(N-epsilon-Isopropyl)-Pro-DAlaNH$_2$ was obtained as trifluoroacetate salt; R$_t$=25.83 min; FAB Mass spec. m/e 1594 (M+H)$^+$. Amino Acid Analysis: 1.00 Ala;. 1.00 Pro; 1.00 Leu; 1.00 Lys; 0.70 NMeTyr; 0.70 Ser.

Example 4

N-Glycolyl-D2Nal-D4ClPhe-D3Pal-Ser-NMeTyr-DCit-Leu-Arg-Pro-DAlaNH$_2$ was obtained as trifluoroacetate salt (34b)

The procedure described in Example 1 was used without the formic acid coupling. After HF cleavage the peptide H-D2Nal-D4ClPhe-D3Pal-Ser-NMeTyr-DCit-Leu-Arg-Pro-DAlaNH$_2$ was reacted with 1.5 equivalents glycolic acid, 1.5 equivalents of dicyclohexylcarbodihnide, and 1.5 equivalents of hydroxybenzotriazole in DMF overnight. The product was precipitated with ether and purified by HPLC, to give NGlycolyl-D2Nal-D4ClPhe-D3Pal-Ser-NMeTyr-DCit-Leu-Arg-Pro-DAlaNH$_2$; R$_2$=21.15 min; FAB Mass spec. m/e 1461 (M+H)$^+$. Amino Acid Analysis: 1.00 Ala; 1.02 Pro; 0.96 Arg; 1.01 Leu; 1.00 Cit; 1.03 NMeTyr; 0.53 Ser; 1.1 D3Pal.

Example 5

The procedure described in Example 1 was used but substituting BOC-DCit for BOC-DLys(Nic), BOC-Arg(Tos) for BOC-Lys(Isp,Cbz) and the appropriate acids for formic acid. After HF treatment, work-up, lyophilization, and HPLC purification the following compounds were obtained:

Example 5a

N-Formyl-D2Nal-D4ClPhe-D3Pal-Ser-NMeTyr-DCit-Leu-Arg-Pro-DAlaNH$_2$ was obtained as trifluoroacetate salt (35b); R$_t$=34.65 min; FAB Mass spec. m/e 1430 (M+H)$^+$. Amino Acid Analysis: 1.00 Ala;. 1.07 Pro; 0.98 Arg;.0.98 Leu; 1.00 Cit; 0.98 NMeTyr; 0.47 Ser; 1.03 D3Pal; 0.99 D4ClPhe.

Example 5b

N-Propionyl-D2Nal-D4ClPhe-D3Pal-Ser-NMeTyr-DCit-Leu-Arg-Pro-DAlaNH$_2$ was obtained as trifluoroacetate salt (36b); R$_t$=37.05 min: FAB Mass spec. m/e 1458 (M+H)$^+$. Amino Acid Analysis: 0.99 Ala;. 1.00 Pro; 0.99 Arg;. 1.02 Leu; 1.00 Cit; 0.97 NMeTyr; (/.47 Ser; 1.04 D3Pal; 1.05 D4ClPhe.

Example 5c

N-Butyryl-D2Nal-D4ClPhe-D3Pal-Ser-NMeTyr-DCit-Leu-Arg-Pro-DAlaNH$_2$ was obtained as trifluoroacetate salt (37b); $R_t$=38.60 min; FAB Mass spec. m/e 1472 (M+H)$^+$. Amino Acid Analysis: 0.99 Ala; .1.00 Pro: 0.99 Arg;.1.02 Leu; 1.00 Cit; 0.94 NMeTyr: 0.46 Ser; 1.00 D3Pal; 0.99 D4ClPhe.

Example 5d

N-Succinamyl-D2Nal-D4ClPhe-D3Pal-Ser-NMeTyr-DCit-Leu-Arg-Pro-DAlaNH$_2$ was obtained as trifluoroacetate salt (38b); $R_t$=35.35 min; FAB Mass spec. m/e 1501 (M+H)$^+$. Amino Acid Analysis :0.99 Ala; .1.00 Pro; 1.00 Arg;.1.02 Leu; 0.91 Cit; 1.00 NMeTyr; 0.49 Ser; 1.14 D3Pal; 1.21 D4ClPhe.

Example 5e

N-Cyclopropylcarbonyl-D2Nal-D4ClPhe-D3Pal-Ser-NMeTyr-DCit-Leu-Arg-ProDAlaNH$_2$ was obtained as trifluoroacetate salt (40b); $R_t$=38.10 min; FAB Mass spec. m/e 1470 (M+H)$^+$. Amino Acid Analysis: 0.97 Ala; 1.01 Pro; 0.97 Arg;. 1.00 Leu; 0.99 Cit; 1.12 NMeTyr; 0.52 Ser; 0.98 D3Pal; 1.05 D4ClPhe.

Example 5f

NPhenylacetyl-D2Nal-D4ClPhe-D3Pal-Ser-NMeTyr-DCit-Leu-Arg-Pro-DAlaNH$_2$ was obtained as trifluoroacetate salt (51b); $R_t$=41.45 min; FAB Mass spec. m/e 1520 (M+H)$^+$. Amino Acid Analysis: 1.00 Ala; 1.03 Pro; 1.03 Arg;.0.96 Leu; 1.01 Cit; 0.77 NMeTyr; 0.48 Ser; 1.15 D3Pal; 1.16 D4ClPhe.

Example 6

N-Succinyl-D2Nal-D4ClPhe-D3Pal-Ser-NMeTyr-DCit-Leu-Arg-Pro-DAlaNH$_2$ (39b)

The procedure described in Example 3 was used but substituting BOC-Cit for BOC-DLys(Nic) and BOC-Arg(Tos) for BOC-Lys(Isp,Cbz). After HF treatment, work-up, lyophilization, and HPLC purification NSuccinyl-D2Nal-D4ClPhe-D3Pal-Ser-NMeTyr-DCit-Leu-Arg-Pro-DAlaNH$_2$ was obtainedm as trifluoroacetate salt; $R_t$=40.0 min; FAB Mass spec. m/e 1502 (M+H)$^+$. Amino Acid Analysis: 1.02 Ala; 1.01 Pro; 0.97 Arg;. 1.00 Leu; 0.99 Cit; 1.12 NMeTyr; 0.52 Ser; 0.98 D3Pal; 1.05 D4ClPhe.

Example 7

N:(Aminocarbonyl)-D2Nal-D4ClPhe-D3 Pal-Ser-NMeTyr-DCit-Leu-Arg-ProDAlaNH$_2$(1c)

In the reaction vessel of a Milligen-Biosearch 9500 peptide synthesizer was placed 1 g (0.6 mmol) of-D-Ala-NH-resin (4-methyl-benzhydrylamine resin). Amino acids were added sequentially according to the following synthetic cycle:

1. Deblocking, to remove the t-BOC group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution for one minute and then the deblocking reaction is run for 20 minutes.
2. Base wash, to remove and neutralize the TFA used for deprotection, is carried out using a solution of 10% N,N'-diisopropylethylamine in methylene chloride. The resin is washed with base three times for one minute each time after a deblocking step.
3. Coupling reaction is carried out using a 3-fold molar excess of 0.3M DMF solution of a t-BOC protected amino acid derivative along with a 3-fold molar excess of 0.3M methylene chloride solution of diisopropylcarbodiimide as activator. The activated amino acid is then coupled to the free alpha amino group of the peptide-resin. The reaction time is as described in the synthesis protocol.
4. Wash, each reaction step is followed by three washes of one minute each: one of methylene chloride, one of (1:1 ) methylene chloride/DMF, and one of DMF.

Synthesis Protocol

The amino protected amino acids are coupled to the resin according the following order, number, and duration of couplings:

| # | Amino Acid | Coupling |
|---|---|---|
| 1. | BOC—Pro | two-1h |
| 2. | BOC—Arg(Tos) | two-1h |
| 3. | BOC—Leu | two-1h |
| 4. | BOC—D—Cit | two-1h |
| 5. | BOC—NMe—Tyr(O-2,6-diCl—Bzl) | two-1h |
| 6. | BOC—Ser(OBzl) | two-1h |
| 7. | BOC—D-3Pal | two-6h |
| 8. | BOC—D-4ClPhe | two-2h |
| 9. | BOC—D2Nal | two-2h |

Upon completion of the synthesis the resin, BOC-D2Nal-D4ClPhe-D3Pal-Ser-NMeTyr(O-2,6-Cl-Bzl)-DCit-Leu-Arg(Tos)-Pro -DAlaNH-resin was deblocked using standard conditions and then reacted with large excess of potassium cyanate in aqueous DMF overnight. The peptide-resin was washed three times with (1:1) DMF/DCM solution and dried overnight over P2O5 under vacuum and then treated with dry HF in the presence of anisole at 0 ° C. for 1 h to cleave the peptide from the resin. The excess of reagent was removed in vacuo. The resin was washed first with ether, then stirred at room temperature with a solution of (1:1:0.1) water/acetonitrile/acetic acid (50 ml) for 15 minutes, and filtered. The flitrate was lyophilized to give the crude peptide as a fluffy powder. This was purified by HPLC using a (25×2.5 cm) Dynamax C-18 column (8 micron) with solvent mixtures varying in a gradient ranging from 89% H$_2$O/11% CH$_3$CN/0.1% TFA over a period of 20 minutes. The UV detector was set at 260 nm. The product was eluted at 25.95 min as a single peak, collected and lyophilized to give pure N-(Aminocarbonyl)D-2Nal-D4ClPhe-D3Pal-Ser-NMeTyr-DCit-Leu-Arg -Pro-DAlaNH$_2$ as the trifluoroacetate salt.: $R_t$=37.80 minutes; FAB Mass spec. m/e 1445 (M+H)$^+$. Amino Acid Anal: 1.02 Ala; 1.02 Pro; 0.97 Arg; 0.98 Leu; 0.98 Cit; 0.59 NMeTyr; 0.52 Ser; 1.01 3Pal; 1.06 4ClPhe.

Example 8

The procedure described in Example 7 was used to obtain the peptide-resin H-D2Nal-D4ClPhe-D3Pal-Ser-NMeTyr(O-2,6-Cl-Bzl)-DCit-Leu-Arg(Tos)-Pro-DAlaNH-resin. This was reacted with large excess of carbonyldiimidazole in DMF for 30 minutes, washed three times with (1:1) DMF/DCM and separately reacted with the appropriate amines in DMF overnight. After HF treatment, workup, HPLC purification, and lyophilization the following compounds were obtained:

Example 8a

N-(Ethylaminocarbonyl)-D2Nal-D4ClPhe-D3Pal-Ser-NMeTyr-DCit-Leu-Arg-ProDAlaNH₂(2c) as the trifluoroacetate salt.: $R_t$=41.40 minutes; FAB Mass spec. m/e 1473 (M+H)⁺. Amino Acid Anal: 1.01 Ala; 0.99 Pro; 1.11 Arg; 0.99 Leu; 0.96 Cit; 0.94 NMeTyr; 0.54 Ser; 1.00 3Pal; 0.98 4ClPhe.

Example 8b

N-(Morpholinocarbonyl)-D2Nal-D4ClPhe-D 3Pal-Ser-NMeTyr-DCit-Leu-Arg-Pro-DAlaNH₂(3c) as the trifluoroacetate salt.: $R_t$=36.75 minutes; FAB Mass spec. m/e 1515 (M+H)⁺. Amino Acid Anal: 1.03 Ala; 1.01 Pro; 0.92 Arg; 1.03 Leu; 1.07 Cit; 0.97 NMeTyr; 0.52 Ser; 0.71 3Pal; 1.02 4ClPhe.

Example 8c

N-(Morpholinoethylaminocarbonyl)-D2Nal-D4ClPhe-D3Pal-Ser-NMeTyr-DCit-Leu-Arg-Pro-DAlaNH₂(4c) as the trifluoroacetate salt.; $R_t$=32.55 minutes; FAB Mass spec. m/e 1558 (M+H)⁺. Amino Acid Anal: 1.01 Ala; 1.03 Pro; 0.96 Arg; 1.00 Leu; 1.00 Cit; 0.78 NMeTyr; 0.41 Set; 1.04 3Pal; 1.09 4ClPhe.

Example 8d

N-(N'-Methylpiperazinylcarbonyl)-D2Nal-D4ClPhe-D3Pal-Ser-NMeTyr-DCit-Leu-Arg-Pro-DAlaNH₂(5c) as the trifluoroacetate salt.; $R_t$=40.27 minutes; FAB Mass spec. m/e 1528 (M+H)⁺. Amino Acid Anal: 1.01 Ala; 1.02 Pro; 0.93 Arg; 1.03 Leu; 1.05 Cit; 1.08 NMeTyr; 0.49 Ser; 0.70 3Pal; 0.87 4ClPhe.

Example 8e

N-(2-Pyridyhnethylaminocarbonyl)-D2Nal-D4ClPhe-D3Pal- Ser-NMeTyr-DCit-Leu-Arg-Pro-DAlaNH₂ (6c) as the trifluoroacetate salt.; $R_t$=33.05 minutes; FAB Mass spec. m/e 1536 (M+H)⁺. Amino Acid Anal: 1.01 Ala; 1.01 Pro; 0.97 Arg; 1.02 Leu; 1.02 Cit; 0.99 NMeTyr; 0.52 Ser; 1.14 3Pal; 1.20 4ClPhe.

Example 8f

N-(3-Pyridyhnethylaminocarbonyl)-D2Nal-D4ClPhe-D3Pal-Ser-NMeTyr-DCit-Leu-Arg-Pro-DAlaNH₂ (7c) as the trifluoroacetate salt.; $R_t$=32.30 minutes; FAB Mass spec. m/e 1536 (M+H)⁺. Amino Acid Anal: 1.02 Ala; 1.03 Pro; 0.96 Arg; 1.00 Leu; 0.99 Cit; 0.82 NMeTyr; 0.40 Ser; 1.04 3Pal; 1.09 4ClPhe.

Example 8g

N-(2-Pyridylethylaminocarbonyl)-D2Nal-D4ClPhe-D3Pal-Ser-NMeTyr-DCit-Leu-Arg-Pro-DAlaNH₂ (8c) as the trifluoroacetate salt.; $R_t$=33.0 minutes; FAB Mass spec. m/e 1550 (M+H)⁺. Amino Acid Anal: 1.01 Ala; 1.03 Pro; 0.96 Arg; 1.02 Leu; 0.98 Cit; 1.00 NMeTyr; 0.51 Ser; 1.11 3Pal; 1.16 4ClPhe.

---

---

What is claimed is:

1. A compound or a pharmaceutically acceptable salt thereof selected from the group consisting of N-Glycolyl-D2Nal-D4ClPhe-D3Pal-Ser-NMeTyr-DCit-Leu-Arg-Pro-DAlaNH₂;

N-Formyl-D2Nal-D4ClPhe-D3Pal-Ser-NMeTyr-DCit-Leu-Arg-Pro-DAlaNH₂;

N -Propionyl-D2Nal-D4ClPhe-D3Pal-Ser-NMeTyr-DCit-Leu-Arg-Pro-DAlaNH₂;

N-Butyryl-D2Nal-D4ClPhe-D3Pal-Ser-NMeTyr-DCit-Leu-Arg-Pro-DAlaNH₂;

N-Succinamyl-D2Nal-D4ClPhe-D3Pal-Ser-NMeTyr-DCit-Leu-Arg-Pro-DAlaNH₂;

N-Formyl-D2Nal-D4ClPhe-D3Pal-Ser-NMeTyr-DLys(Nicotinyl)-Leu-Lys(N-epsilon-lsopropyl)-Pro-DAlaNH₂;

N-Propionyl-D2Nal-D4ClPhe-D3Pal-Ser-NMeTyr-DLys(N-epsilon-Nicotinyl)-Leu-Lys(N-epsilon-Isopropyl)-Pro-D AlaNH₂;

N-Butyryl-D2Nal-D4ClPhe-D3Pal-Ser-NMeTyr-DLys(N-epsilon-Nicotinyl)-Leu-Lys(N-epsilon-Isopropyl)-Pro-DAlaNH₂; and N-Cyanoacetyl-D2Nal-D4ClPhe-D3Pal-Ser-NMeTyr-DLys(N-epsilon-Nicotinyl)-Leu-Lys(N-epsilon-Isopropyl)-Pro-DAlaNH₂.

* * * * *

UNITED STATES PATENT AND TRADEMARK OFFICE
CERTIFICATE OF CORRECTION

PATENT NO. : 5,413,990  Page 1 of 4
DATED : May 9, 1995
INVENTOR(S) : F. HAVIV; T. D. FITZPATRICK; R. E. SWENSON; C. J. NICHOLAS; N. A. MORT It is certified that error appears in the above-indentified patent and that said Letters Patent is hereby corrected as shown below:

COLUMN 3, LINE 9: delete "icitrullyl, D-omocitrullyl and insert --D-citrullyl, D-homocitrullyl--

COLUMN 4, LINE 11: delete "an-finoacyl" and insert --aminoacyl--

COLUMN 4, LINE 39: delete "marrunal" and insert --mammal--

COLUMN 5, LINE 20: delete "Cahno" and insert --Cahn--

COLUMN 5, LINE 53: after "phenyl)alanine" delete --s--

COLUMN 5, LINE 56: delete "L-2-amino-(6-aminocarbonylanfino)hexanoic" and insert -- L-2-amino-(6-aminocarbonylamino)hexanoic--

COLUMN 6, LINE 15: delete "antide" and insert --amide"

COLUMN 7, LINE 1: delete "N-Phenyl  acetyl-D2Nal-" and insert --N-Phenylacetyl-D2Nal- --

COLUMN 8, LINE 55: delete "intramnuscular" and insert --intramuscular--

COLUMN 10, LINE 30: delete "an-fino" and insert --amino--

UNITED STATES PATENT AND TRADEMARK OFFICE
CERTIFICATE OF CORRECTION

PATENT NO. : 5,413,990
DATED : May 9, 1995
INVENTOR(S) : F. HAVIV; T. D. FITZPATRICK; R. E. SWENSON; C. J. NICHOLAS; N. A. MORT

It is certified that error appears in the above-indentified patent and that said Letters Patent is hereby corrected as shown below:

| | |
|---|---|
| COLUMN 10, LINE 36: | delete "antino" and insert --amino-- |
| COLUMN 10, LINE 68: | delete "bcnzyloxycarbonyl" and insert --benzyloxycarbonyl-- |
| COLUMN 11, LINE 4: | delete "9-fluorenyhnethyloxycarbonyl" and insert -- 9-fluorenylmethyloxycarbonyl-- |
| COLUMN 11, LINE 8: | after amino delete"s". |
| COLUMN 12, LINE 41: | after is delete "o" |
| COLUMN 15, LINE 20: | delete "N,N'- " and insert --N,N- -- |
| COLUMN 15, LINE 27: | delete "propylcarbodimide" and insert --propylcarbodiimide-- |
| COLUMN 16, LINE 33: | delete ".0.99" and insert --0.99-- |
| COLUMN 16, LINE 51: | detele ".1.02" and insert --1.02-- |
| COLUMN 17, LINE 10: | delete ".0.98" and insert --0.98-- |
| COLUMN 17, LINE 19: | delete ".0.99 " and insert --0.99-- |

UNITED STATES PATENT AND TRADEMARK OFFICE
CERTIFICATE OF CORRECTION

PATENT NO. : 5,413,990
DATED : May 9, 1995
INVENTOR(S) : F. HAVIV; T. D. FITZPATRICK; R. E. SWENSON; C. J. NICHOLAS; N. A. MORT

It is certified that error appears in the above-indentified patent and that said Letters Patent is hereby corrected as shown below:

| | |
|---|---|
| COLUMN 17, LINE 36: | delete "16 11" and insert --1611-- |
| COLUMN 17, LINE 45: | delete ".1.01" and insert --1.01-- |
| COLUMN 18, LINE 3: | delete ".0.98" and insert --0.98-- |
| COLUMN 18, LINE 8: | delete "1sopropyl." and insert --Isopropyl-- |
| COLUMN 18, LINE 37: | delete "ylcarbodihnide" and insert --ylcarbodiimide-- |
| COLUMN 18, LINE 67: | delete "(/.47" and insert --0.47-- |
| COLUMN 19, LINE 6: | delete ".1.00" and insert --1.00-- |
| COLUMN 19, LINE 15: | delete ".1.00" and insert --1.00-- |
| COLUMN 19, LINE 15: | delete ".1.02" and insert --1.02-- |
| COLUMN 19, LINE 32: | delete "D3Pal" and insert --D3Pal-- |
| COLUMN 19, LINE 43: | delete "obtainedm" and insert --obtained-- |

UNITED STATES PATENT AND TRADEMARK OFFICE
CERTIFICATE OF CORRECTION

PATENT NO. : 5,413,990
DATED : May 9, 1995
INVENTOR(S) : F. HAVIV; T. D. FITZPATRICK; R. E. SWENSON; C. J. NICHOLAS; N. A. MORT

It is certified that error appears in the above-indentified patent and that said Letters Patent is hereby corrected as shown below:

COLUMN 20, LINE 37: delete "P205" and insert --$P_2O_5$--

COLUMN 21, LINE 63: delete "N-(2-Pyridyhnethylaminocarbonyl)" and insert --N-(2-Pyridylmethylaminocarbonyl)--

COLUMN 22, LINE 3: delete "Pyridyhneethylaminocarbonyl" with --Pyridylmethylaminocarbonyl--

Signed and Sealed this

Twenty-sixth Day of September, 1995

Attest:

BRUCE LEHMAN

Attesting Officer    Commissioner of Patents and Trademarks

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="Xaa at position 1 is a 5-oxo-prolyl aminoacyl residue."

(xi) SEQUENCE DESCRIPTION: SEQ ID NO:1:

Xaa His Trp Ser Tyr Gly Leu Arg Pro Gly
  1             5                      10